(12) United States Patent
Clive-Smith et al.

(10) Patent No.: US 11,957,827 B2
(45) Date of Patent: Apr. 16, 2024

(54) SYSTEM AND METHOD FOR CALIBRATING A CENTRIFUGE

(71) Applicant: Entia Limited, London (GB)

(72) Inventors: Millie Clive-Smith, London (GB); Toby Basey-Fisher, London (GB)

(73) Assignee: Entia Limited, London (GB)

( * ) Notice: Subject to any disclaimer, the term of this patent is extended or adjusted under 35 U.S.C. 154(b) by 1393 days.

(21) Appl. No.: 16/343,950

(22) PCT Filed: Oct. 10, 2017

(86) PCT No.: PCT/GB2017/053055
§ 371 (c)(1),
(2) Date: Apr. 22, 2019

(87) PCT Pub. No.: WO2018/078325
PCT Pub. Date: May 3, 2018

(65) Prior Publication Data
US 2020/0054819 A1    Feb. 20, 2020

(30) Foreign Application Priority Data
Oct. 24, 2016  (GB) ...................... 1617939

(51) Int. Cl.
*A61M 1/36*  (2006.01)
*B01D 17/02*  (2006.01)
(Continued)

(52) U.S. Cl.
CPC ....... *A61M 1/3693* (2013.01); *B01D 17/0217* (2013.01); *B01L 3/502753* (2013.01);
(Continued)

(58) Field of Classification Search
CPC ........ A61M 1/3693; A61M 2205/3306; A61M 2205/70; B01D 17/0217; B01L 3/502753;
(Continued)

(56) References Cited

U.S. PATENT DOCUMENTS 6,002,474 A * 12/1999 Thomas ............... G01N 15/042
356/244

FOREIGN PATENT DOCUMENTS

| WO | 96017243 A1 | 6/1996 | |
| WO | WO-9617243 A1 * | 6/1996 | ........... G01N 15/042 |
| WO | 01032289 A1 | 5/2001 | |

OTHER PUBLICATIONS

International Search Report and Written Opinion for Application No. PCT/GB2017/053055 dated Jan. 3, 2018 (10 pages).

* cited by examiner

*Primary Examiner* — Walter D. Griffin
*Assistant Examiner* — Shuyi S. Liu
(74) *Attorney, Agent, or Firm* — Michael Best & Friedrich LLP (57) ABSTRACT

A sample holder for use in a centrifuge, the sample holder being generally planar and comprising: an aperture or recess for releasably retaining a sample storage member including a sample chamber adapted to contain a volume of liquid; a centre point around which the holder will rotate during use; and one or more calibration features, wherein the calibration feature(s) comprise one or more outer edges, which lie on the side of the or each calibration feature which is furthest from the centre point, and the one or more outer edges comprise a series of radially spaced-apart outer edge portions or positions which are spaced at different distances from the centre point as a function of angular position around the centre point.

18 Claims, 6 Drawing Sheets

(51) Int. Cl.
  *B01L 3/00* (2006.01)
  *B04B 5/04* (2006.01)
  *G01N 15/00* (2006.01)
  *G01N 15/04* (2006.01)
  *G01N 15/05* (2006.01)
  *G01N 33/49* (2006.01)

(52) U.S. Cl.
  CPC ......... *B04B 5/0407* (2013.01); *G01N 15/042* (2013.01); *G01N 15/05* (2013.01); *G01N 33/49* (2013.01); *A61M 2205/3306* (2013.01); *A61M 2205/70* (2013.01); *B01L 2300/0803* (2013.01); *B01L 2400/0409* (2013.01); *G01N 2015/0065* (2013.01); *G01N 2015/045* (2013.01)

(58) Field of Classification Search
  CPC ..... B01L 2300/0803; B01L 2400/0409; B01L 2200/0621; B01L 2300/0864; B04B 5/0407; B04B 5/00; B04B 5/04; B04B 13/00; G01N 15/042; G01N 15/05; G01N 33/49; G01N 2015/0065; G01N 2015/045; G01N 2021/5969; G01N 2015/047; G01N 2015/055; G01N 2021/5973; G01N 21/07; G01N 33/491
  See application file for complete search history.

SYSTEM AND METHOD FOR CALIBRATING A CENTRIFUGE

CROSS-REFERENCE TO RELATED APPLICATION DATA

This application is a U.S. national phase entry of International Application No. PCT/GB2017/053055, filed Oct. 10, 2017, which claims priority to GB Patent Application No. 1617939.2, filed Oct. 24, 2016, the entire contents of which are incorporated herein by reference in their entirety.

DESCRIPTION OF INVENTION

This invention relates to a system and method for fluid analysis, and in particular relates to a system for the accurate analysis of fluids under centrifugation.

When analysing a multi-component liquid such as blood, one known technique involves placing a sample of the fluid in an elongate sample chamber of a cuvette, and rotating the cuvette in a centrifuge, such that the elongate sample chamber is arranged generally radially with respect to the axis about which the cuvette rotates.

As the skilled reader will understand, under the forces arising from the centrifugation process, the heaviest components of the fluid will gather at the end of the sample chamber which is furthest the axis of rotation, while the lightest components will gather at the end of the sample chamber that is closest to the axis of rotation. In this way, fractionation of the fluid can be achieved, and the boundaries between the various components can be measured.

For instance, a medical professional may wish to determine the proportion of red blood cells in a sample of blood, haematocrit.

During the centrifugation process, the red blood cells will (being the heaviest component of the blood) gather at the location furthest from the axis of rotation. Assuming the blood sample is within a sample chamber of fixed dimensions in a radial direction from the axis of rotation, the highest position of the layer of the red blood cells (edge) relative to the end of the sample chamber furthest from the axis of rotation divided by the position of the total sample height (edge) relative to the end of the sample chamber furthest from the axis of rotation can be used to indicate the proportion of red blood cells in the sample (haematocrit).

Figure 1:
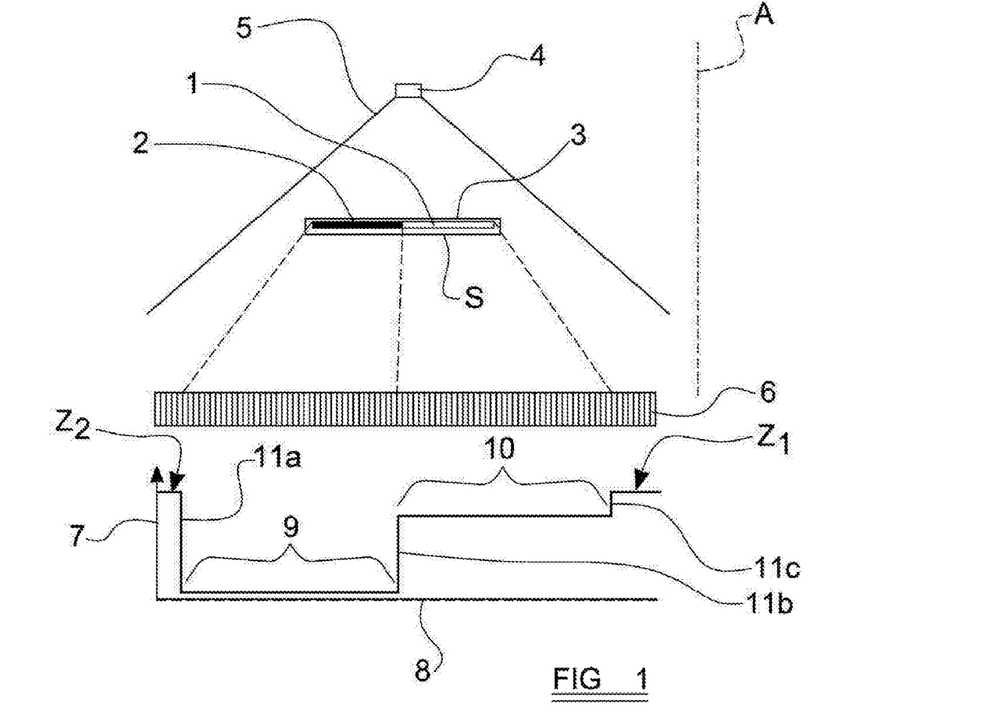
FIG. 1 shows a conventional measurement system.

With reference to FIG. 1 of the accompanying drawings, a schematic view is shown of a conventional set up for analysing blood under these circumstances. A blood sample 1 is held within an elongate sample chamber S, which is subject to centrifugation. As discussed above, the blood sample 1 has separated into two separate components, namely the red blood cells 2, which have accumulated at the end of the sample chamber which is furthest from the axis of rotation A, and the remaining components 3 of the blood occupy the part of the sample chamber that is closest to the axis of rotation.

A radiation source 4 is provided to one side of the sample chamber. The radiation source 4 emits a beam 5 of radiation (which may be optical frequencies of light, or any other type of radiation), which impinges on the blood sample 1.

A sensor array 6 is provided on the far side of the blood sample 1 from the radiation source 4. The sensor array 6 includes a number of discrete radiation sensors, arranged along an axis which is aligned with the blood sample 1. It will be understood that the beam 5 of radiation emitted by the radiation source 4 will impinge from the blood sample 1, and to the extent that the radiation passes through the blood sample 1, this radiation will be detected by the sensors in the sensor array 6.

The sensor array 6 may, for example, comprise a narrow, elongate charge coupled device (CCD).

The lower portion of FIG. 1 shows a graph representing schematically the intensity of radiation 7 detected by the sensor array 6 along its length 8. In an innermost zone $Z_1$, and in an outermost zone $Z_2$, the radiation bypasses the blood sample 1 and impinges directly on the sensor array 6. Where the beam 5 of radiation passes through the red blood cells 2, there is a corresponding zone 9, which extends to an outer edge 11a which meets the outermost zone $Z_2$, where the intensity of radiation detected by the sensor array 6 is low, since relatively little radiation will be transmitted through the dense red blood cells 2. Where the radiation passes through the other components 3 of the blood, there will be a region 10, which extends to an inner edge 11c which meets the innermost zone $Z_1$, where the level of radiation detected by the sensor array 6 will be relatively high, since these other parts of the blood will be more transmissive than the red blood cells 2.

Where these two regions 9,10 meet each other there will be an edge 11b in the graph of detected radiation. In analysis of the blood sample 1, the length of the zone 9 created by the red blood cell component (or 11b-11a) as a portion of the intensity profile created by total length of the sample (i.e. the total of the two regions 9, 10 or 11c-11a) provides a non-linear though direct indication of the proportion of red blood cells 2 in the blood sample 1.

Figure 2:
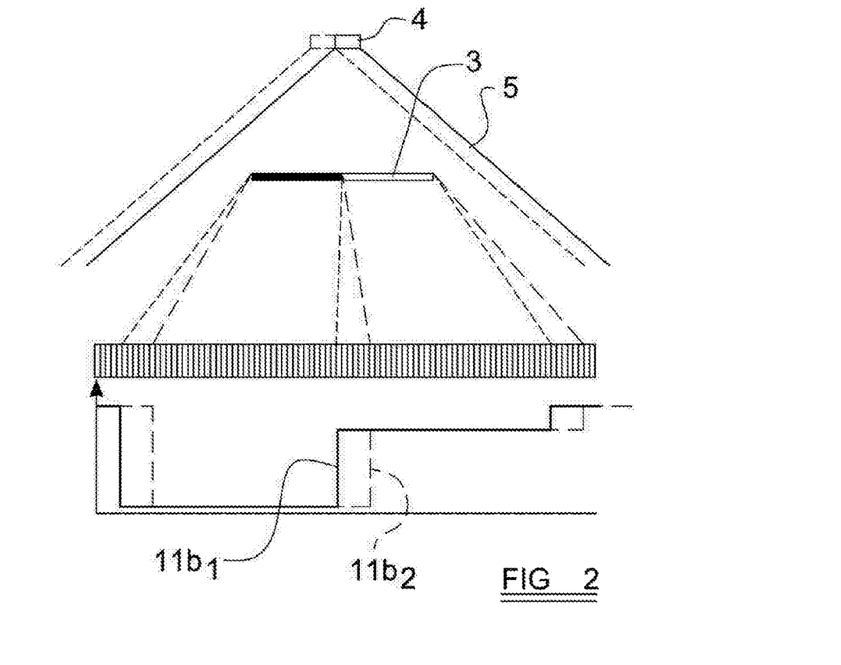
FIG. 2 shows the measurement system of FIG. 1 after dislodgement of the radiation source from its correct position.

However, for the system shown in FIG. 1, accurate determination of the red blood cells as a portion of the total sample depends on a consistent spatial relationship between the radiation source 4, the vessel (such as a cuvette) that holds the blood sample 1, and the sensor array 6. If any one or more of these components is moved or is dislodged from its original alignment, accuracy in the system will be lost. FIG. 2 shows the system of FIG. 1 in solid lines, with an alternative laterally dislodged position for the radiation source 4 being shown in dashed lines. It can be seen that the beam 5 of radiation produced by the radiation source 4 will also be laterally shifted as a result of this. A lateral shift in the radiation source would lead edges 11a, 11b and 11c to change with a non-linear relation to each other that would make direct indication of the proportion of red blood cells 2 in the blood sample 1 inaccurate.

If the radiation source 4 had not been shifted in this way, the edge detected by the sensor array 6 would be at the position indicated by reference numeral in FIG. 2. Instead, as a result of the shift, the position of this edge is detected at position $11b_2$. This reading will therefore not be accurately comparable to readings taken when the system was properly calibrated, as shown in FIG. 1.

SUMMARY OF THE INVENTION

It is an object of the present invention to provide an improved system for analysing fluid.

Accordingly, one aspect of the present invention provides a sample holder for use in a centrifuge, the sample holder being generally planar and comprising:

an aperture or recess for releasably retaining a sample storage member including a sample chamber adapted to contain a volume of liquid; a centre point around which the holder will rotate during use; and one or more calibration features, wherein the calibration feature(s) comprise one or more outer edges, which lie on the side of the or each calibration feature which is furthest from the centre point, and the one or more outer edges comprise a series of radially spaced-apart outer edge portions or positions which are spaced at different distances from the centre point as a function of angular position around the centre point.

Advantageously, the sample holder comprises a calibration feature having a continuous outer edge which has a plurality of outer edge portions or positions which are at varying distances from the centre point.

Preferably, the outer edge of the calibration feature is curved and the distance of the outer edge from the centre point varies continuously or substantially continuously along its length.

Conveniently, the outer edge of the calibration feature comprising a series of discrete outer edge portions, each of which is at a different distance from the centre point.

Advantageously, the sample holder comprises a series of individual, spaced-apart calibration features, each feature having an outer edge which is at a different distance from the centre point.

Preferably, each calibration feature is substantially elongate and arranged to extend in a substantially radial direction with respect to the centre point.

Conveniently, each calibration feature is substantially circular.

Advantageously, the or each calibration feature is an aperture formed through the entire thickness of the holder.

Preferably, the or each calibration feature comprises a reflective element provided on a surface of the holder.

Conveniently, the calibration features further comprise one or more inner edges, which lie on the side of the or each calibration feature which is closest to the centre point, and the one or more inner edges comprise a series of radially spaced-apart inner edge portions or positions which are spaced at different distances from the centre point as a function of angular position around the centre point.

Another aspect of the present invention provides a sample holder according to any of the above in combination with a sample containment member which is adapted to be receivably retained in the aperture or recess of the sample holder, the sample containment member including a sample chamber in which, during use, a fluid to be analysed may be contained.

Advantageously, the sample chamber has a length which, in use, is arranged to lie in a substantially radial direction with respect to the centre point, and wherein the outer edge portions or positions of calibration feature(s) correspond to distances from the centre point that lie along the length of the sample chamber.

Preferably, the outer edge of the or each one calibration feature is at a depth, with respect to the depth of the sample holder, which is the same or substantially the same as the depth at which fluid in the sample chamber of the sample containment member will lie when the sample containment member is retained in the aperture or recess of the sample holder.

Conveniently, the outer edge of the or each one calibration feature has a thickness which is the same or substantially the same as the thickness of fluid in the sample chamber of the sample containment member, when the sample containment member is retained in the aperture or recess of the sample holder and the sample chamber is filled with fluid.

A further aspect of the present invention provides a centrifuge apparatus comprising: a sample holder and sample containment member according to any of the above; a rotation arrangement adapted to hold the sample holder and rotate the sample holder around the centre point thereof; a radiation source which is arranged to be on one side of the sample holder; and a radiation detector, adapted to detect radiation emitted by the radiation source, and arranged on the opposite side of the sample holder from the light source, or on the same side of the holder as the radiation source.

Advantageously, the centrifuge apparatus comprises an elongate array of radiation sources arranged along a line which is substantially radial with respect to the centre of the sample holder and extending over a radial distance which corresponds to, or is greater than, the radial extent of the sample chamber.

Preferably, the centrifuge apparatus comprises a elongate array of radiation detectors, arranged in a line which is substantially radial with respect to the centre of the sample holder, and arranged over a distance which corresponds to, or is greater than, that of the sample chamber.

Another aspect of the present invention provides a method of calibration and analysis comprising the steps of: providing a centrifuge apparatus according to any of the above; providing a fluid sample in the sample chamber of the sample containment member; rotating the sample holder using the rotation arrangement; illuminating the radiation source, and, during illumination of the radiation source, recording an intensity profile for each outer edge portion or position of the calibration feature(s), comprising signals received from the radiation detector when radiation from the radiation source is transmitted through, or reflected from, the calibration feature(s); illuminating the radiation source, and, during illumination of the radiation source, recording an intensity profile for the fluid sample, comprising signals received from the radiation sensor when radiation from the radiation source is transmitted through, or reflected from, the fluid sample; and determining the position of at least one boundary between phases in the fluid sample, based on correlation between a feature in the intensity profile of the fluid sample corresponding to the boundary, and features in the intensity profiles relating to one or more of the outer edge portions or positions of the calibration feature(s).

Conveniently, a plurality of radiation sources are provided, and recording an intensity profile for each, or a selection of, the outer edge portions or positions of the calibration feature(s), and recording an intensity profile for the fluid sample, is carried out for each one of the radiation sources illuminated in turn.

Advantageously, the method further comprises the steps of: during illumination of the radiation source, recording an intensity profile for each inner edge portion or position of the calibration feature(s), comprising signals received from the radiation detector when radiation from the radiation source is transmitted through, or reflected from, the calibration feature(s); and determining the position of at least one boundary between phases in the fluid sample, based on correlation between a feature in the intensity profile of the fluid sample corresponding to the boundary, and features in the intensity profiles relating to one or more of the inner edge portions or positions of the calibration feature(s).

A further aspect of the present invention provides a sample holder for use in a centrifuge, the sample holder being generally planar and comprising: an aperture or recess for releasably retaining a sample storage member including a sample chamber adapted to contain a volume of liquid; a centre point around which the holder will rotate during use; and one or more calibration features, wherein the calibration feature(s) comprise one or more inner edges, which lie on the side on the or each calibration feature which is closest to the centre point, and the one or more inner edges have a series of radially spaced-apart edge portions or positions which are spaced at different distances from the centre point.

Preferably, the sample holder is generally planar and comprises: an aperture or recess for releasably retaining a sample storage member including a sample chamber adapted to contain a volume of liquid; a centre point around which the holder will rotate during use; one or more first calibration features, wherein the first calibration feature(s) comprise one or more outer edges, which lie on the side of the or each first calibration feature which is furthest from the centre point, and the one or more outer edges comprise a series of radially spaced-apart outer edge portions or positions which are spaced at different distances from the centre point; and one or more second calibration features, wherein the second calibration feature(s) comprise one or more inner edges, which lie on the side on the or each second calibration feature which is closest to the centre point, and the one or more inner edges have a series of radially spaced-apart edge portions or positions which are spaced at different distances from the centre point.

BRIEF DESCRIPTION OF THE DRAWINGS

In order that the invention may be more readily understood, embodiments thereof will now be described, by way of example, with reference to the accompanying drawings, in which.

DETAILED DESCRIPTION

Figure 3:
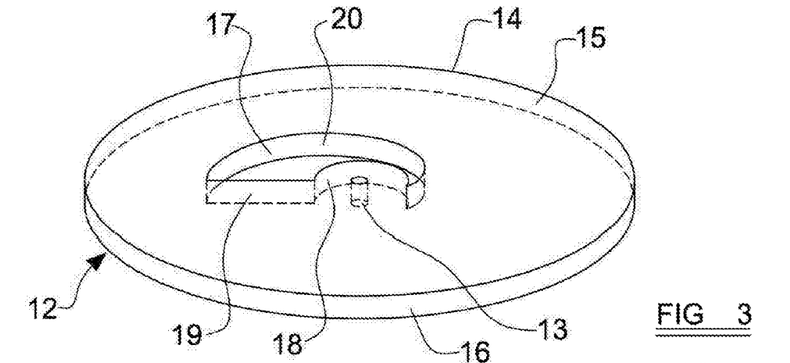
FIGS. 3, 4 and 5 show a disc having a calibration aperture.

Referring to FIG. 3, a disc 12 is shown. The disc 12 includes a central mounting aperture 13, which is aligned with the centre of the disc 12, and preferably passes throughout the entire thickness of the disc 12. In the example shown the mounting aperture 13 is generally circular in cross-section, although the mounting aperture can take any suitable shape.

The disc has top and bottom surfaces 14, 15, which are substantially flat and parallel with one another, and a circumferential side wall 16.

A calibration aperture 17 is formed through the disc 12. The calibration aperture 17 is formed through the entire thickness of the disc 12, and the inner edges of the calibration aperture 17 are (in this example) generally straight, i.e. passing directly from the top surface 14 to the bottom surface 15 in a direction which is perpendicular with the plane of the disc 12.

The calibration aperture 17 includes an inner edge 18, which is concentric or substantially concentric with the centre of the disc 12. In the example shown, the inner edge 18 extends for approximately 180° around the centre of the disc 12, at a distance which is, in the depicted embodiment, about one tenth of the way from the centre of the disc 12 to the outer edge thereof. For the purposes of accurate calibration, it is preferable for the calibration aperture 17 to extend at least 180° around the disc 12, although the invention is not limited to this.

A spacing edge 19 extends from one end of the inner edge 18. The spacing edge 19 is straight, and extends directly or substantially directly radially outwardly from the centre of the disc 12 towards the outer edge thereof. The length of the spacing edge 19 is, in the example shown, around one third of the total radius of the disc 12.

Finally, the calibration aperture 17 has an outer edge 20, which is curved and extends from the other end 21 of the inner edge 18 to the outer end 22 of the spacing edge 19.

The outer edge 20 of the calibration aperture 17 is shaped as follows. Where the outer edge 20 meets the inner edge 18, these edges 18, 20 converge at a point, and at this point the effective distance between the inner and outer edges 18, 20 is zero.

As the outer edge 20 is followed along its length, the radial distance between the inner and outer edges 18, 20 (i.e. the distance between the inner and outer edges 18, 20, measured in a straight line passing directly radially outwardly from the centre of the disc 12 towards its edge) increases linearly (i.e. by the same amount for each unit of angular distance) until the outer edge 20 meets the outer point of the spacing wall 19, at which point the radial distance between the inner and outer edges 18, 20 is identical to the length of the spacing wall 19.

Figure 4:
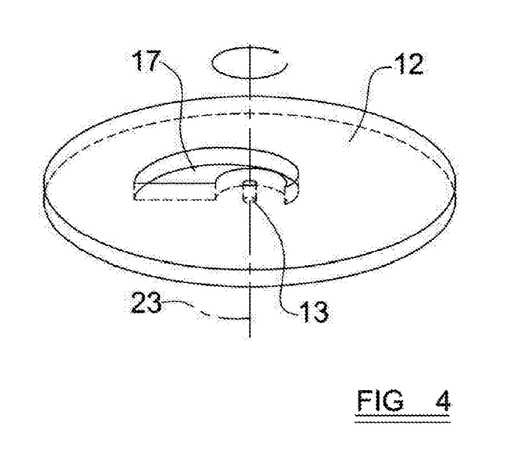
Figure 5:
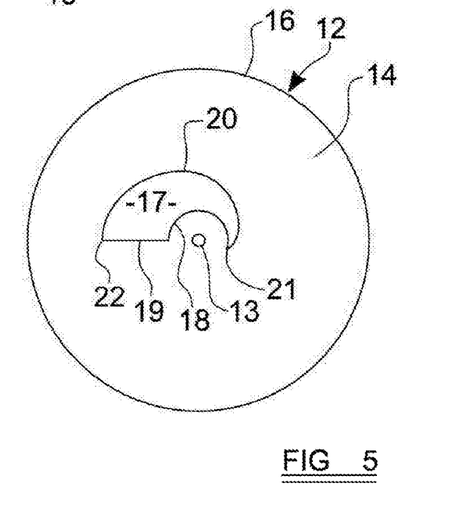

FIG. 4 shows the disc 12 mounted for rotation around an axis 23, which passes through the mounting aperture 13, and is perpendicular to the plane of the disc 12. In FIG. 4, an arrow represents the fact that, in use, the disc 12 will rotate around the axis 23.

Figure 6:
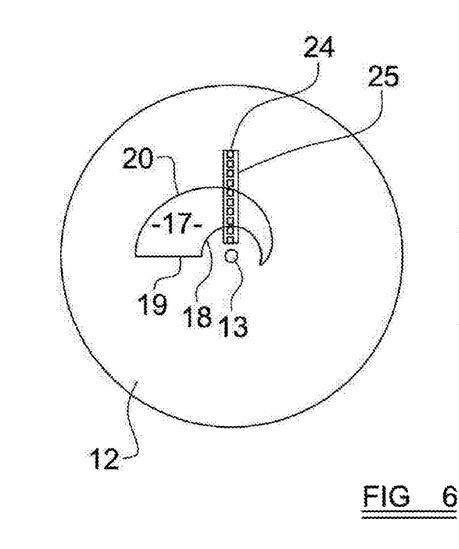
FIGS. 6 and 7 shows the disc of FIGS. 3, 4, and 5 in a centrifuge setup.
Figure 7:
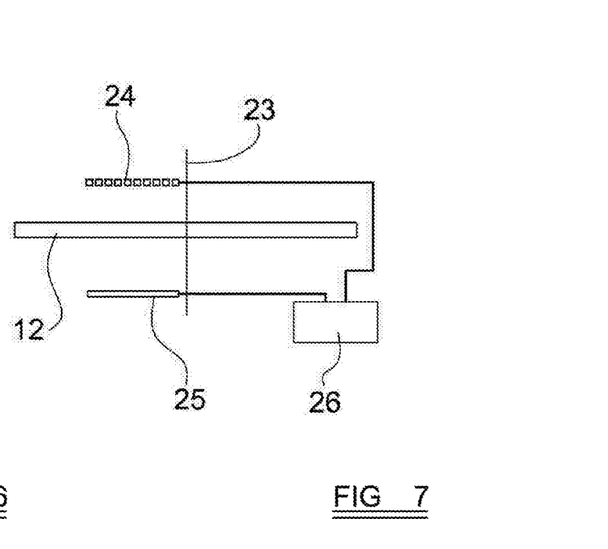

With reference to FIGS. 6 and 7, the disc 12 may be mounted for rotation around the axis 23, with a plurality of light sources 24 being positioned on one side of the disc 12, and an elongate light receiving array 25 being positioned on the other side of the disc 12. The plurality of light sources 24 are arranged so that, looking at the disc 12 along the axis of rotation 23, the light sources 24 are arranged in a line which is radial with respect to the disc 12. The line of light sources 24 extends from a point between the mounting aperture 13 of the disc 12 and the inner edge 18 of the calibration aperture 17, outwardly to a position which is further from the mounting aperture 13 than the furthest end of the spacing edge 19. The light sources 24 are, therefore, when viewed along the axis of rotation 23, arranged in a line which extends radially on one side of the centre of the disc 12. The elongate light receiving array 25 is arranged to be directly or substantially directly opposite the light sources 24.

The disc 12 is preferably comprised of a material that is opaque to the radiation emitted by the light sources 24.

If the disc 12 is rotated to a position in which any part of the calibration aperture 17 is aligned between the light sources 24 and the light receiving array 25, light from one or more of the light sources 24 may pass through the calibration aperture 17 and be received by the light receiving array 25. If, on the other hand, the disc 12 is rotated to a position where no part of the calibration aperture 17 is aligned between the light sources 24 and the light receiving array 25, then the light from the sources 24 will be blocked from reaching the light receiving array 25.

It should be understood that, in the setup shown in FIG. 7, the light sources 24 and light receiving array 25 remain stationary, while the disc 12 rotates around the axis 23. The light sources 24 and light receiving array 25 are connected to a processor 26, which sends control signals to the light sources 24, and receives signals from the light receiving array 25.

Figure 8A:
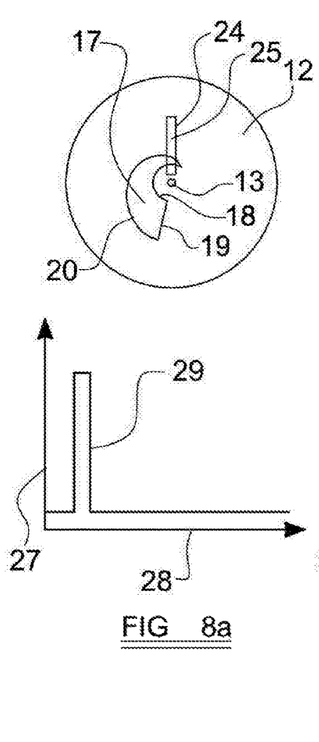
FIGS. 8a-8c show different rotational positons of the disc of FIGS. 3, 4, and 5 with respect to the other components of the centrifuge setup and intensity profiles.
Figure 8B:
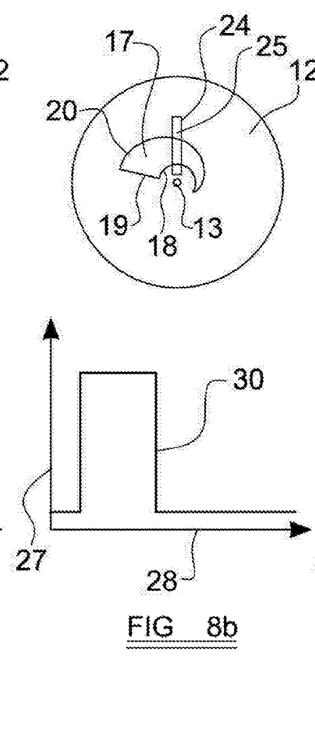
Figure 8C:
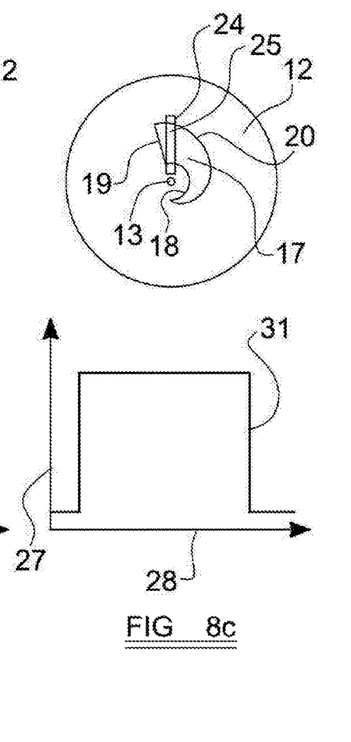

FIGS. 8a, 8b, and 8c show the disc 12 in three different rotational orientations with respect to the light sources 24 and light receiving array 25. Below each of FIGS. 8a, 8b and 8c is a graph showing schematically the light intensity 27 received by the light receiving array 25, as a function of distance 28 along its length, passing from the inner end thereof to the outer end.

FIG. 8a shows a rotational position in which a relatively narrow part of the calibration aperture 17 overlaps with the light sources 24 and light receiving array 25. It can be seen that the intensity profile for this position comprises a relatively narrow peak 29.

FIG. 8b shows a position when the disc 12 has rotated (in this example, clockwise) with respect to the position shown in 8a, so that the light sources 24 and light receiving array 25 overlap with a wider part of the calibration aperture 17, near the middle thereof. It can be seen that the intensity profile for this position comprises a wider peak 30.

Finally, FIG. 8c shows the position where the disc 12 has rotated so that the light sources 24 and light receiving array 25 overlap with a wide part of the calibration aperture 24, close to the spacing edge 19.

As would be expected, the intensity profile for this position comprises a peak 31 that is wider than the peaks 29, 30 that appear for the other rotational positions.

With regard to the overlap of the calibration aperture 17 with the light sources 24 and light receiving array 25, as the disc 12 rotates the inner edge 18 of the calibration aperture 17 is effectively radially stationary with respect to the light sources 24 and light receiving array 25. However, during rotation of the disc 12 with respect to the light sources 24 and light receiving array 25, the outer edge 20 of the calibration aperture appears to move steadily from an initial position that is close to the inner edge 18 (as shown in FIG. 8a), away from the inner edge 18 until it is at a maximum distance therefrom, near the spacing aperture 19 (as shown in FIG. 8c).

Figure 9:
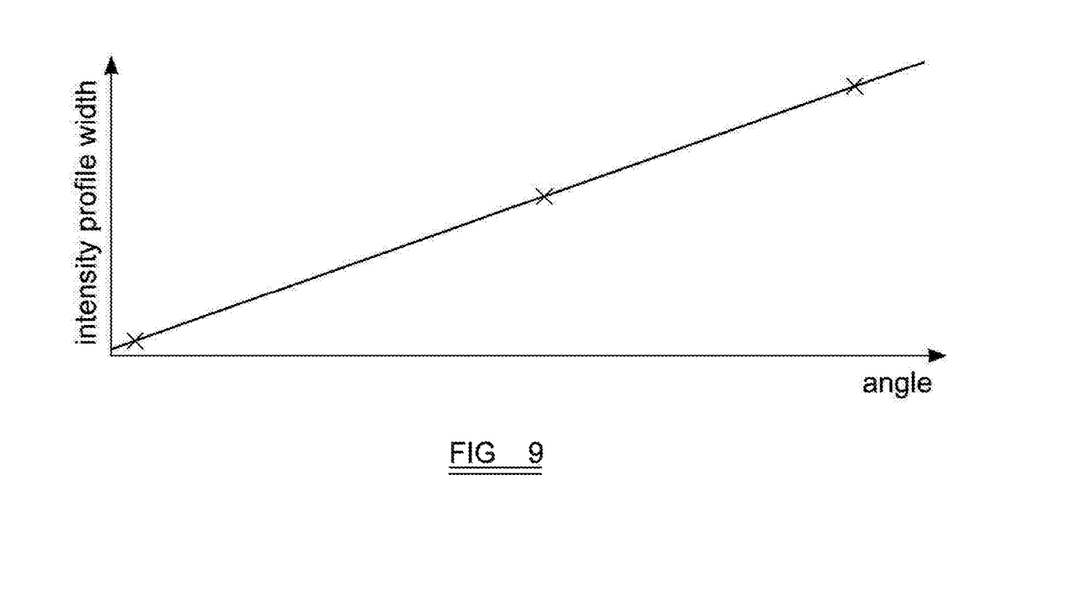
FIG. 9 shows a schematic graph of intensity profile width measured in the rotational positions of FIG. 8a-8c.

FIG. 9 schematically shows how the width of the intensity profile increases linearly as the angle of the disc 12 changes. It will be understood that the graph shown in FIG. 9 covers the portion of rotation of the disc 12 in which at least some part of the calibration aperture 17 overlaps with the light sources 24 and light receiving array 25. At angular positions where no part of the calibration apertures 17 overlaps in this way, then zero or substantially zero light from the light sources 24 will be detected by the light receiving array 25.

Figure 10:
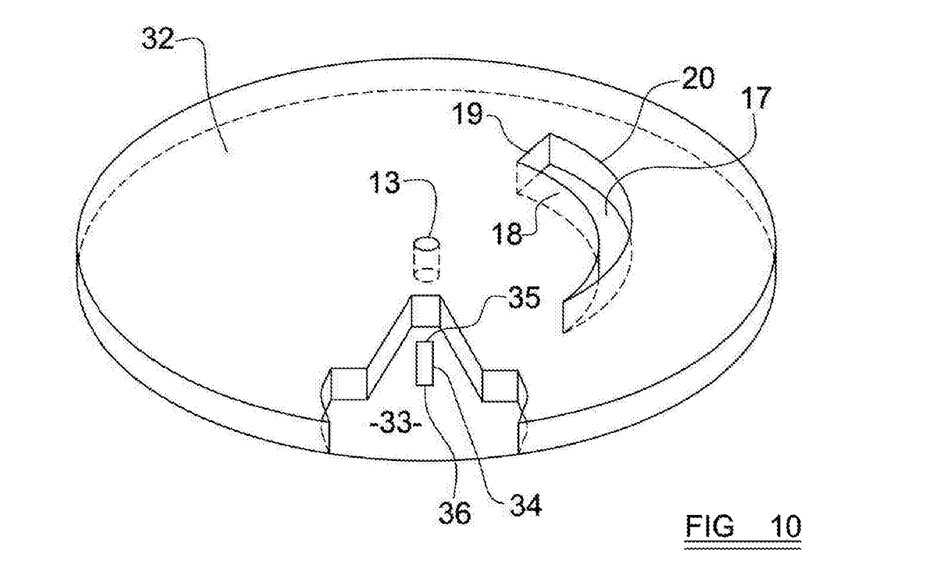
FIGS. 10 and 11 shows a disc suitable for use with the present invention.
Figure 11:
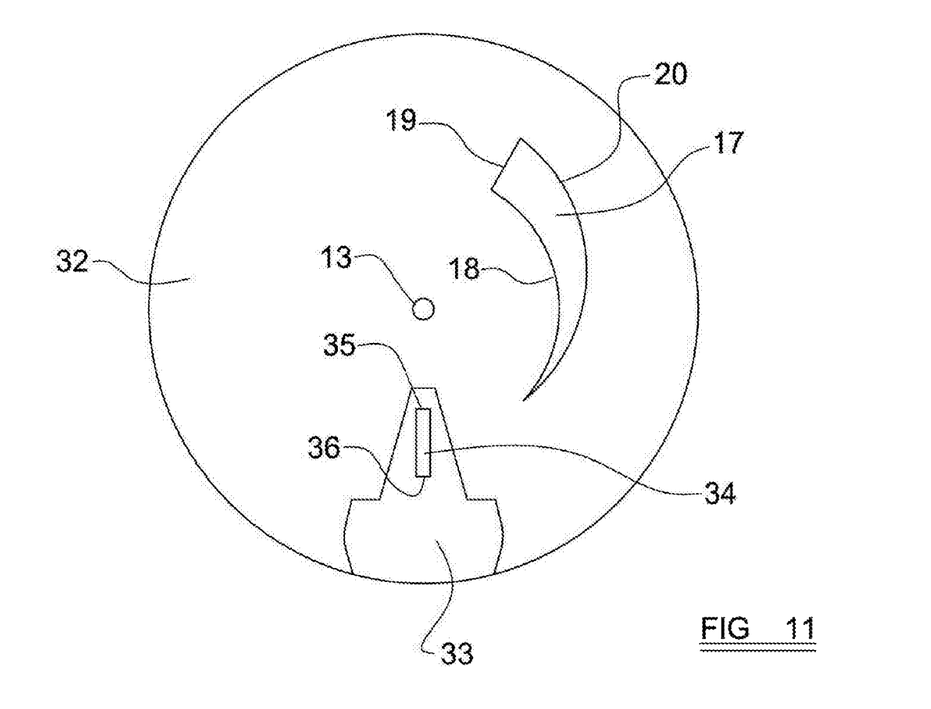

FIGS. 10 and 11 show a further disc 32 which includes a calibration aperture 17 including an inner wall 18, outer wall 20 and a spacing wall 19 as described above. Once again, the further disc 32 has a central mounting aperture 13, on which the disc 32 may be mounted for rotation about an axis.

The further disc 32 also includes a holding aperture 33, for releasably retaining a cuvette or other device which holds a sample of fluid to be analysed. The overall shape of the holding aperture 33 will depend upon the shape of the cuvette other device which is to be used with the disc 32, and it is expected that the shape of the holding aperture 33 will generally match the exterior shape of the cuvette or other device. In this example, the holding aperture 33 is formed at the edge of the disc 32, and extends generally inwards towards (but does not reach) the central mounting aperture 13.

Marked on FIGS. 10 and 11 is the location 34 where a sample chamber of the cuvette will be located. In this example, the sample chamber will be arranged generally radially with respect to the disc 32, and extends between an inner end 35, which is set a radius $r_1$ from the centre of the disc 32, and an outer end 36, which is set at a distance $r_2$ from the centre of the disc 32.

The calibration aperture 17 is formed in the disc 32 such that the inner edge 18 thereof, is at a distance which is equal to, or less than, $r_1$ from the centre of the disc 32. At the widest point of the calibration aperture 17, the outer edge 20 lies at a distance which is substantially equal to, or greater than, $r_2$ from the centre of the disc 32. The skilled reader will understand that, therefore, the length of the spacing wall 19 is roughly equal to the length the sample chamber.

Steps in a method of fluid analysis using the further disc 32 will now be described. In this example, blood is the fluid to be analysed. A sample of blood is loaded into a cuvette in known fashion. The cuvette is then fixed in place in the holding aperture 33, so that its sample chamber lies in the position 34 indicated in FIGS. 10 and 11. The disc 32 is then rotated about its axis. Any suitable rotation rate may be used, although one example of a suitable rate is 6,000 rpm.

As a result of this rotation, a radially outwardly-directed force will act on the blood held in the sample chamber of the cuvette. The heaviest components of the blood, i.e. the red blood cells, will gather at the end of the sample chamber which is furthest from the axis of rotation. The lighter components of the blood (e.g. serum) will collect at the end of the sample chamber that is closest to the axis of rotation.

A calibration stage of the apparatus is then carried out.

As discussed above, an array of light sources is arranged to be on one side of the disc 32, and an array of light sensors is placed in a corresponding location on the opposite side of the disc 32. In a first step, one of the light sources in the array is illuminated. This may be, for example, the innermost light source in the array. While this first light source is illuminated, the signals from the light sensors are analysed at several different rotational positions in which the calibration aperture 17 is aligned between the light sensors and the light sources. For instance, a reading may be taken when the narrowest part of the calibration aperture 17 is aligned between the light sources and the light sensors. Ten or twenty (for example) readings may then be taken at spaced-apart angular positions, culminating in a final reading when the widest part of the calibration aperture 17 is aligned between the light sources and the light sensors.

The signals gathered from the light sensors at each of these rotational positions are stored, to generate an intensity profile for the light source that is illuminated. To ensure that the stored intensity profile is accurate repeated intensity profiles may be taken during different rotations of the disc 32. For instance, ten readings may be taken.

As a next step, the first light source is extinguished and a second light source is illuminated.

The above process is repeated, in that signals from the light sensors are gathered at several different rotational orientations of the calibration aperture 17 with respect to the light sources and light sensors.

This process is repeated, with each of the light sources being illuminated in turn. A convenient way of carrying this step out may be to illuminate each light source in turn beginning at the innermost light source and working towards the outermost light source, or vice versa. However, the light sources can be illuminated in any sequence.

Following this calibration stage, a measurement stage begins.

Once again, a first one of the light sources is illuminated, with the other light sources being extinguished. The signals from the light sensors are gathered as the analysis chamber is aligned between the light sources and the light sensors. This may be repeated, for instance, ten times.

Following this, the first light source is extinguished and a second light source is illuminated, and this measurement process is repeated. As for the calibration stage, each of the light sources is illuminated in turn, and the signals gathered by the light sensors are received when the analysis chamber is positioned between the light sources and the light sensors.

As discussed above, under centrifugation the blood in the sample chamber will separate into two main phases, namely a relatively opaque phase comprising the blood red cells, and a relatively transmissive phase comprising the other components of the blood, such as serum. Between these two phases there will be an "edge". Effectively, the red blood cells of the blood sample will cast a shadow on the light sensing array, with the edge of this shadow being an indicator of the position where the red blood cells in the blood sample terminate.

During the calibration stage, information is gathered regarding the position in which the edge of the shadow falls when the outer edge 20 of the calibration aperture 17 is positioned at various radial distances from the centre of the disc 32, i.e. various distances along the length of the light sensing array. For each of the intensity profiles gathered during the calibration stage, the distance of the outer edge 20 of the calibration aperture 17 from the centre of the disc 32 is known—the rotational position of the disc 32 at each calibration point is known, and the shape of the outer edge 20 of the calibration aperture 17 is also known.

As discussed above, the outer edge 20 of the calibration aperture 17 in this example is continuously curved, and so does not have clearly demarked edge regions at different distances from the centre of the disc 32. However, calibration readings are taken at set angular positions of the disc 32, where these angular positions are spaced apart from each other.

Once the intensity profile arising from a blood sample has been gathered, this intensity profile can then be compared to the intensity profiles that were gathered during the calibration stage.

As discussed above, the intensity profile arising from the blood sample will include edges, indicating the position where the red cells start and terminate and the serum terminates. These edges can be compared to the edge that appears in the data from each of the calibration stages. Where the position of the edge in the intensity profile arising from the blood sample is the same as the position of the edge in an intensity profile from the calibration stage, it can be concluded that the position of the point where the red blood cells of the blood sample end, as a function of distance from the centre of the disc 32, is the same as the position of the outer edge 20 of the calibration aperture 17, in the rotational position corresponding to that calibration stage, again as a function of distance from the centre of disc 32. The same is true of the start of the red blood cells and the serum/air boundary.

As an alternative, where the position of the edge arising from a blood sample falls halfway between the position of the edges in the intensity profiles of two calibration steps, an interpolation process can be used to determine the position of the termination of the red blood cells in the blood sample, compared to the positions of the edges in the two calibration stages. For instance, if the edge arising from the blood sample falls halfway between the edges in the two calibration stages, it may be concluded that the position of the termination of the red cells lies halfway between the positions of the outer edge 20 of the calibration aperture 17 in the two appropriate calibration steps.

The skilled reader will understand that this method eliminates many possible sources of error that might arise from mis-calibration. Because the cuvette is held rigidly in place with respect to the calibration aperture, the spatial relation between the cuvette and the calibration aperture is fixed. This means that any errors arising from misalignment of the disc 32 itself, the light sources and/or the light sensors will be compensated for—the calibration stage will correctly register the position of the outer edge of the calibration aperture at various rotational positions, and this data can then be applied to the signal derived during analysis of the blood sample. Any errors or variation in the relative positions of various components will therefore automatically be corrected for.

Although not shown in the figures, the disc 32 may have timing features thereon to assist the apparatus in determining the angular position of the disc 32 during rotation. For instance, the disc 32 may have three evenly angularly-spaced notches formed therethrough, with these notches being provided at known angular locations with respect both to the holding aperture 33 and the calibration aperture 17. As the disc 32 rotates, the light sensing array will receive three "flashes" of light at evenly-spaced time intervals, and the system will then be able to determine the rotational orientation of the disc 32. The use of features of this kind to determine the rotational orientation of a disc during centrifugation is known per se and will not be discussed in detail here.

Figure 12A:
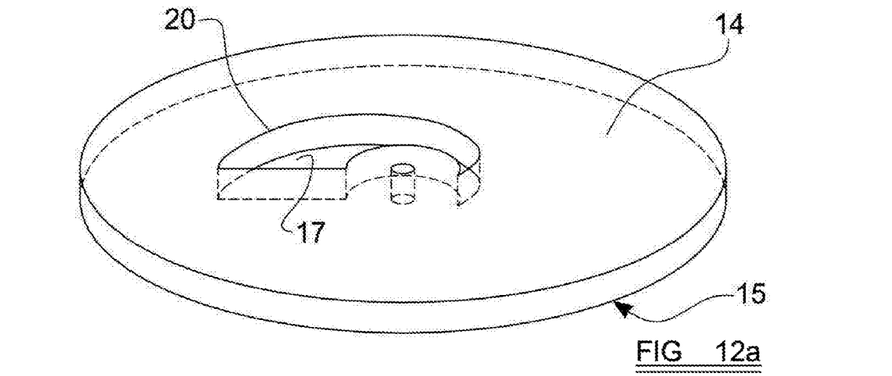
FIGS. 12a, 12b and 13a-13f show different cross-sectional profiles for calibration apertures suitable for use with the present invention.
Figure 12B:
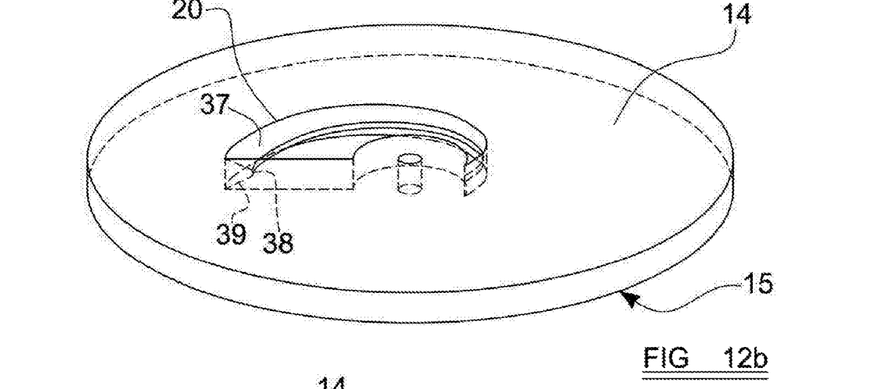

FIGS. 12a and 12b show different cross-sectional shapes for the outer edge 20 of the calibration aperture 17. FIG. 12a shows the calibration aperture 17 as discussed above, in which the outer edge 20 thereof is straight in cross-section, passing directly from the top surface to the bottom surface of the disc, and being aligned perpendicular or substantially perpendicular to the plane of the disc. In another embodiment, as shown in FIG. 12b, the outer edge 20 has a cross-sectional shape having an upper wall 37 which slopes, as it passes from the top surface 14 towards the bottom surface 15, in a direction which is towards the centre of the disc 32. The upper wall 37 terminates slightly above the midpoint of the thickness of the disc 32. A middle wall 38 is preferably relatively short and protrudes directly from the end of the upper wall 37 towards the bottom surface 15 of the disc 32, in a direction which is perpendicular or substantially perpendicular to the plane of the disc 32.

Extending from the lower end of middle wall 38 is a lower wall 39. As the lower wall 39 passes from the middle wall 38 to the bottom surface 15 of the disc 32, the lower wall 39 slopes in a direction away from the centre of the disc 32.

Preferably, the cross-sectional profile of the outer wall 20 in this embodiment is symmetrical or substantially symmetrical around a plane which lies halfway through the thickness of the disc 32.

It will be appreciated that this alternative shape for the outer edge 20 of the calibration aperture 17 provides a relatively thin edge.

In embodiments where the cross-sectional shape of the outer edge 20 of the calibration aperture 17 is of this shape, the sample chamber of the cuvette, that holds the sample under analysis, is set to be at the same position with respect to the depth of the disc as the middle wall 38. This ensures that the shadow cast by the middle wall 38 on the light sensing array can be compared accurately to the shadow that is cast by the fluid sample held within the sample chamber. The thickness of the middle wall 38, in the depth direction of the disc 32, may also be the same, or substantially the same, as the thickness of a blood sample held within the sample chamber. This will mean that the shadow cast by the middle wall 38 will be as directly comparable as possible to the shadow cast by fluid in the sample chamber.

FIGS. 13*a*-13*f* show potential cross-sectional shapes for the outer edge 20 of the calibration aperture 17.

Figures 13A, 13D:
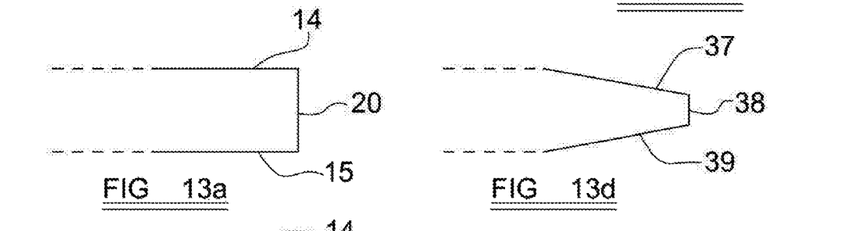

FIG. 13*a* shows a straight cross-sectional shape with squared edges, corresponding to the shape shown in FIGS. 3-6, 10, 11 and 12*a*.

Figures 13B, 13E:
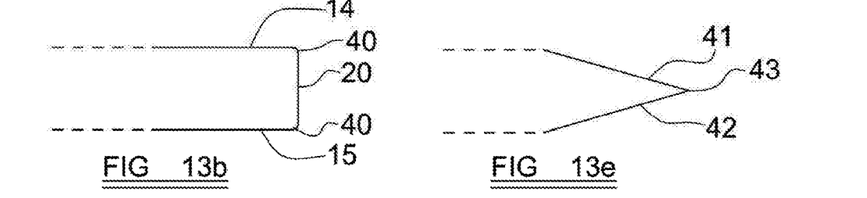

FIG. 13*b* shows a shape which is similar to that shown in 13*a*, although where the outer edge 20 meets the upper and lower surfaces 14, 15 of the disc 32 there are rounded or radiused edges 40.

Figure 14A:
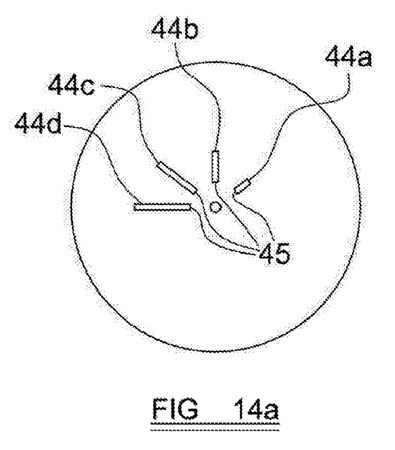
FIGS. 14a-14f show various calibration apertures suitable for use with the present invention.
Figure 14B:
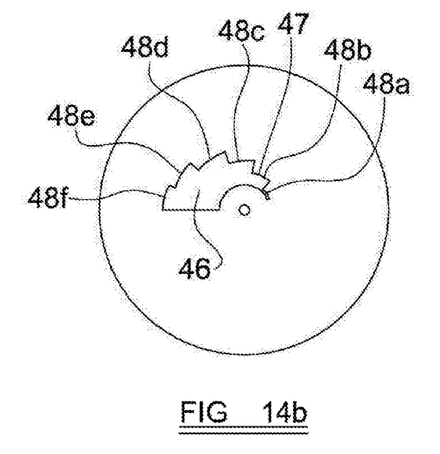
Figure 14C:
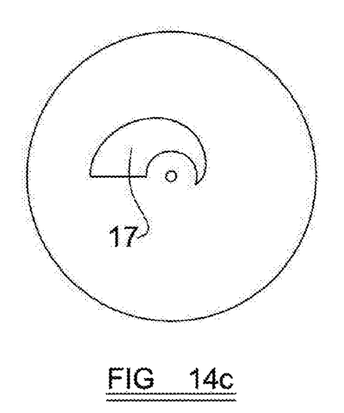

FIG. 14*c* shows further alternative in which the profile of the outer edge 20 is rounded and approximately semi-circular.

FIG. 12*d* shows the profile shown in FIG. 12*b*, involving upper and lower walls 37, 39, with a middle wall 38 therebetween.

FIG. 12*e* shows a further alternative, similar to that shown in FIG. 12*d*, although the upper and lower walls 41, 42 are not separated by a middle wall, and converge at a sharp point 43

Figures 13C, 13F:
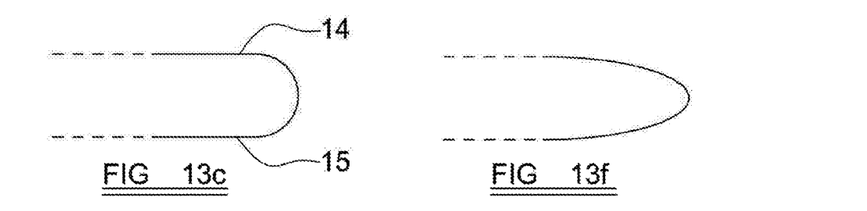

Finally FIG. 12*f* shows a further alternative in which the profile of the outer edge 20 is curved in a parabolic manner, thereby presenting a more pointed edge than the example shown in FIG. 13*c*.

The skilled reader will appreciate that other cross-sectional shapes for the outer edge 20 are possible, and the invention is not limited to the examples shown herein.

FIGS. 14*a*-14*f* show different calibration apertures that are suitable for use with the present invention.

With reference firstly to 14*a*, a disc is shown which, instead of having a single calibration aperture, has four separate calibration apertures 44*a*-44*d*. Each of the calibration apertures 44*a*-44*d* has an inner edge 45 which lies at the same distance from the centre of the disc. Each of the calibration apertures 44*a*-44*d* is generally rectangular and elongate, extending radially directly away from the centre of the disc. However, a first one 44*a* of the calibration apertures is relatively short, terminating at a first distance from the centre of the disc. A second one 44*b* of the calibration apertures is longer, terminating at a greater distance from the centre of the disc. A third one 44*c* of the calibration apertures is longer still, terminated at a third distance from the centre of the disc, which is greater than the second distance. Finally, a fourth one 44*d* of the apertures is longest, terminating a fourth distance from the centre of the disc, which is greater than the other three distances. In use, the inner edges 45 of the calibration apertures 44*a*-44*d* will lie at a distance which is the same as, or slightly less than, the distance of the inner end of the sample chamber from the centre of the disc. The outer end of the fourth calibration aperture 44*d* in the centre of the disc will be at approximately the same, or slightly more than, the distance at which the outer end of the sample chamber lies from the centre of the disc.

The skilled reader will understand that these separate calibration apertures 44*a*-44*d* will function in a similar way to the single calibration aperture 17 discussed above. The outer ends of each of the apertures 44*a*-44*d* will cast respective shadows on the array of light sensors at different positions, thus allowing calibration of the system which can subsequently be used in analysing a blood sample, or sample of other liquid held in the sample chamber.

FIG. 14*b* shows an alternative shape for a single calibration aperture 46, having an outer edge 47 which has several (in this example, six) connected calibration edges 48*a*-48*f*, each of which is concentric with the centre of the disc. The calibration edges 48*a*-48*f* are connected by radially-extending connecting edges.

The calibration edges 48*a*-48*f* are preferably set at steadily-increasing radial distances from the centre of the disc.

The skilled reader will understand that this calibration aperture 46 works in a similar manner to the calibration aperture 17 shown in FIG. 3. However, a difference is that, as the disc rotates, each of the calibration edges 48*a*-48*f* will cast, for a length of time, a shadow which remains stationary, thus allowing a more robust and accurate and determination of where the shadow falls on the light sensing array, relating to each the calibration edges 48*a*-48*f*. This example therefore has clearly demarked edge regions or portions 48*a*-48*f*, set at different linear distances from the centre of the disc.

FIG. 14*c* shows a calibration aperture 17 as shown in FIG. 3 and elsewhere.

Figure 14D:
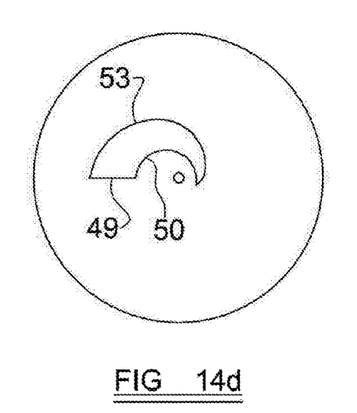

FIG. 14*d* shows an alternative aperture 49, which is similar in shape to the calibration aperture 17 shown in FIG. 3, although in this case the inner edge 50 of the calibration aperture 49 is not concentric with the centre of the disc.

This aperture 49 therefore has both an inner edge 50 and an outer edge 53 that continuously vary in distance from the centre of the disc. This aperture 49 could therefore be used to obtain calibration information based on the outer edge and, separately, on the inner edge. This is explained in more detail below.

Figure 14E:
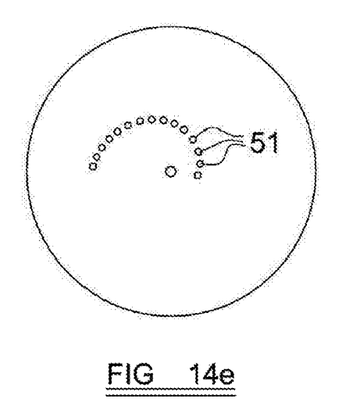

FIG. 14*e* shows an alternative set of calibration apertures 51, each of which comprises a circular or substantially circular aperture formed through the depth of the disc. The apertures 51 are evenly radially spaced around the centre of the disc. A first one of the apertures 51 is provided at a first distance from the centre of the disc. Each successive aperture is provided at a distance which is incrementally greater than the previous one, cumulating in a final aperture 51 which is at a greatest distance from the centre of the disc.

It will be understood that these apertures 51 function in a similar manner in the apertures 44*a*-44*d* shown in FIG. 14*a*. The outer edge of each of the apertures 51 is at a known location, and casts a shadow on the light-sensing array as the aperture 51 passes between the light sources and the light sensing array.

Figure 14F:
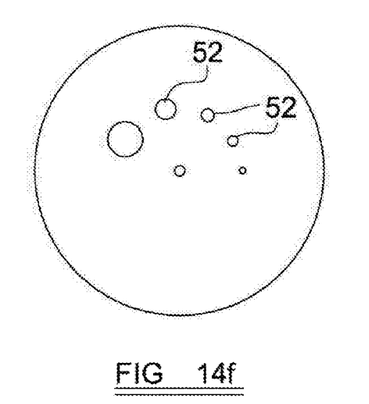

Finally, FIG. 14*f* shows a further set of calibration apertures 52, which are again circular or substantially circular apertures which are formed through the depth of the disc. In this example, the apertures are evenly radially spaced around the centre of the disc. The centres of the apertures are all located at the same or substantially the same radial distance from the centre of the disc. However, the radii of the apertures increase steadily from a first aperture 52, which has the smallest radius, to a final one of the apertures 52, which has the greatest radius. It will be understood that the outer edge of each aperture 52 will be located at an increasing distance from the centre of the disc, and each edge will therefore cast a shadow on the light sensitive array in a different position, corresponding to a known outer edge position.

As will be apparent from these diverse examples, there are many different shapes for calibration aperture(s) that can be used with the present invention. What is important is that the calibration aperture(s) provide an outer edge or series of outer edges which, as the disc rotates, are at different known distances from the centre of the disc. The calibration aperture(s) will ideally present a range of outer edges, or a single shaped outer edge, which are at, or have parts thereof at, different radial distances from the centre of the disc, extending between a relatively short distance, being equal to or less than the radial distance at which the inner edge of the sample chamber will lie in use (or, alternatively, equal to or less than the smallest distance from the centre of the disc at which an edge to be observed can be expected to lie), and a greatest distance, corresponding to a position which is equal to or greater than the position where the outer end of the sample chamber will lie during use (or, alternatively, equal to or more than the greatest distance from the centre of the disc at which an edge to be observed can be expected to lie). This provision of outer edges at various positions will allow the system to calibrate accurately where the shadow arising from each edge falls, and the information gathered from this calibration can then be used to analyse in an accurate manner the boundaries between various fractions, phases or components in a liquid under analysis in the sample chamber.

In the embodiments discussed thus far (aside from the one shown in FIG. 14d), it is only the shadow cast by an outer edge of a calibration aperture that is used for calibration purposes. This technique will be useful where, for instance in the analysis of the proportion of red blood cells in a blood sample, a measurement is to be taken of the volume occupied by the heaviest or most dense fraction in a liquid.

In other embodiments, however, the invention may be used to determine the volume occupied by the lightest or least dense fraction in a multi-phase liquid. In this case, one or more calibration apertures could be provided in which the distance of the inner edge of each aperture varies from the centre of the disc varies, and the shadow cast on the light sensing array by the inner edge or edges is analysed to provide calibration for later analysis of a fluid sample. In these embodiments, the outer edge of the or each calibration aperture may be radially stationary with respect to the centre of the disc. The skilled reader will readily appreciate how the techniques discussed above may be adapted to be applied to the circumstances.

As a further possibility, it may be desired to observe the inner and outer limits of an intermediate fractional component of the fluid under analysis, i.e. a component which is neither the most dense nor the least dense. In this case, the edge that appears at the inner limit of this fractional component and the edge that appears at the outer limit of the fractional component may need to be determined.

In this embodiment, two separate calibration apertures may be provided through the disc, one of which has a stationary inner edge and an outer edge whose distance from the centre of the disc varies (as shown in FIG. 3), and a second calibration aperture which has a stationary outer edge, and an inner edge whose distance varies from the centre of the disc. In use of a disc of this kind, two separate calibration stages may be carried out, one to detect the shadows cast by the outer edge of the first calibration aperture, and a second one to detect shadows cast by the inner edge of the second calibration aperture. Following this, two separate analysis stages may take place, one to measure the inner edge by the fractional component of the liquid under analysis and a second, separate analysis stage to detect the position of the shadow cast by the outer edge of the component or fraction under analysis. Alternatively, both the inner and outer edges may be detected in a single calibration stage and/or the inner and outer edges of the fractional component under analysis may be detected in a single measurement stage.

Of course, instead of one calibration aperture for each of the inner and outer edges, a set of calibration apertures (for instance, as shown in FIGS. 14a, 14e and 14f) may be provided for either or both of the inner or outer edges.

As a further alternative, as shown in FIG. 14d, both the inner edge 50 and the outer edge 53 of the same aperture 49 may be used for calibration purposes. Embodiments of the invention may, at a minimum, use only one single aperture to obtain calibration information for both inner and outer edges. The skilled reader will understand how this may be applied to the other types of aperture disclosed herein. For example, as a variation of the apertures shown in FIG. 14a, the linear distances of the inner edges 45 of the respective apertures may vary from the centre of the disc, as well as (as is the case in FIG. 14a) the linear distances of the outer edges 44a-44d of the apertures from the centre of the disc varying.

In the above discussion, the calibration stage is carried out and completed before the measurement of a blood sample takes place. However, the skilled reader will appreciate that there is no reason for these steps to occur in this order. What is important is that, for each of the light sources in the array, the light source is illuminated and an intensity profile for the calibration aperture(s), and for the fluid sample, is gathered. The intensity profile from the fluid sample may equally be gathered before the intensity profiles from the calibration aperture(s) are obtained.

Indeed, in preferred embodiments, each of the light sources is illuminated, and while the light source is illuminated intensity profiles are gathered both from the calibration aperture(s) and from the fluid sample. This allows measurements to be made for calibration purposes, and measurements of the fluid sample to be made, in an efficient manner.

In the above discussion, the element which has the calibration aperture(s) formed therethrough, and which holds the fluid sample, is referred to as a disc. However, there is no reason why the outer edge of this element needs to be circular and this element can take any suitable shape.

The above discussion refers to calibration apertures as holes formed through the entire depth of the disc. It is envisaged that the disc may be formed from a material which is opaque to the radiation produced by the light or radiation sources, and that each calibration aperture may comprise a region of the disc which is transparent or substantially transparent to the radiation. This may comprise, for example, an insert of a transparent material which is placed into a hole in the disc. It should therefore be understood that the term "calibration aperture" requires a region of the disc through which the radiation can pass unimpeded or substantially unimpeded, and that this does not necessarily require a physical hole passing through the disc.

In the above discussion, the light sensing array is positioned on the opposite side of the disc from the light sources. The information gathered by the light sensing array therefore provides an indication of the transmission of light from the light sources through the fluid in the sample chamber. It is also envisaged that this technique could be used with the measurement of reflectivity, i.e. the light sensing array is placed on the same side of the disc as the light sources, and the light gathered by the light sensing array is indicative of the light reflected by the sample in the sample chamber.

In these embodiments, it is envisaged that, instead of a calibration aperture, one or more reflective elements such as mirrors may be placed on, or incorporated into, the surface of the disc that faces the light sources and the light sensing array. The light reflecting element(s) may be shaped in the same way as the calibration apertures discussed above. The light reflecting elements may also be incorporated into the disc so that the reflecting surface(s) thereof lie at the same depth as a fluid sample held by a cuvette or other sample container which is to be used with the disc. During a calibration phase, light will be reflected from the reflective element(s), and an illumination profile or reflection profile can then be gathered for each light source at various positions of the outer edge of the reflective element(s). This can then be compared to the illumination or reflection profiles received during analysis of a fluid sample, in a way that will be readily be understood by the skilled reader.

The skilled reader will appreciate that embodiments of the invention provide robust and reliable methods for analysing multi-phase liquids, that will confer significant advantages with respect to conventional techniques.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A sample holder for use in a centrifuge, the sample holder being generally planar and comprising:
    an aperture or recess for releasably retaining a sample storage member including a sample chamber adapted to contain a volume of liquid;
    a centre point around which the holder will rotate during use; and
    one or more calibration features, wherein the calibration feature(s) comprise one or more outer edges, which lie on the side of the or each calibration feature which is furthest from the centre point, and the one or more outer edges comprise a series of radially spaced-apart outer edge portions or positions which are spaced at different distances from the centre point as a function of angular position around the centre point, and wherein each of the one or more calibration features is an aperture formed through an entire thickness of the holder or is an insert of a transparent or substantially transparent material which is placed into a hole in the holder.

2. A sample holder according to claim 1, wherein the calibration feature(s) has a continuous outer edge which has a plurality of outer edge portions or positions which are at varying distances from the centre point.

3. A sample holder according to claim 2, wherein the outer edge of the calibration feature(s) is curved and the distance of the outer edge from the centre point varies continuously or substantially continuously along its length.

4. A sample holder according to claim 2, wherein the outer edge of the calibration feature(s) comprising a series of discrete outer edge portions, each of which is at a different distance from the centre point.

5. A sample holder according to claim 1, comprising a series of individual, spaced-apart calibration features, each feature having an outer edge which is at a different distance from the centre point.

6. A sample holder according to claim 5, wherein each calibration feature is substantially elongate and arranged to extend in a substantially radial direction with respect to the centre point.

7. A sample holder according to claim 5, wherein each calibration feature is substantially circular.

8. A sample holder according to claim 1, wherein the calibration features further comprise one or more inner edges, which lie on the side of the or each calibration feature which is closest to the centre point, and the one or more inner edges comprise a series of radially spaced-apart inner edge portions or positions which are spaced at different distances from the centre point as a function of angular position around the centre point.

9. A sample holder according to claim 1 in combination with a sample containment member which is adapted to be receivably retained in the aperture or recess of the sample holder, the sample containment member including a sample chamber in which, during use, a fluid to be analysed may be contained.

10. A sample holder and sample containment member according to claim 9, wherein the sample chamber has a length which, in use, is arranged to lie in a substantially radial direction with respect to the centre point, and wherein the outer edge portions or positions of calibration feature(s) correspond to distances from the centre point that lie along the length of the sample chamber.

11. A sample holder and sample containment member according to claim 9, wherein the outer edge of the or each one calibration feature is at a depth, with respect to the depth of the sample holder, which is the same or substantially the same as the depth at which fluid in the sample chamber of the sample containment member will lie when the sample containment member is retained in an aperture or recess of the sample holder.

12. A sample holder and sample containment member according to claim 9, wherein the outer edge of the or each calibration feature has a thickness which is the same or substantially the same as the thickness of fluid in the sample chamber of the sample containment member, when the sample containment member is retained in an aperture or recess of the sample holder and the sample chamber is filled with fluid.

13. The sample holder of claim 1, wherein the calibrations feature(s) comprise an inner edge which lies on the side of the calibration feature which is closest to the centre point, and wherein the inner edge is concentric with the centre point.

14. A sample holder for use in a centrifuge, the sample holder being generally planar and comprising:
    an aperture or recess for releasably retaining a sample storage member including a sample chamber adapted to contain a volume of liquid;
    a centre point defining an axis of rotation around which the holder will rotate during use; and
    one or more calibration features, wherein the calibration feature(s) comprise one or more outer edges, which lie on the side of the or each calibration feature which is furthest from the centre point, and the one or more outer edges comprise a series of radially spaced-apart outer edge portions or positions which are spaced at different distances from the centre point as a function of angular position around the centre point, wherein each of the one or more calibration features is an aperture formed through an entire thickness of the holder or is an insert of a transparent or substantially transparent material which is placed into a hole in the holder, and wherein at least one of the one or more outer edges includes a cross-sectional shape taken parallel to the axis of rotation, and wherein at least a portion of the cross-sectional shape is not parallel to the axis of rotation.

15. The sample holder of claim 14, wherein at least a portion of the cross-sectional shape is any one of semi-circular, curved, wedge-shaped, truncated wedge-shaped, and parabolic in shape.

16. The sample holder of claim 14, wherein a majority of the cross-sectional shape is not parallel to the axis of rotation.

17. A sample holder for use in a centrifuge, the sample holder being generally planar and comprising:

an aperture or recess for releasably retaining a sample storage member including a sample chamber adapted to contain a volume of liquid;

a centre point around which the holder will rotate during use;

a plurality of calibration features, wherein each calibration feature includes a respective outer edge which lies on the side of the calibration feature which is furthest from the centre point, and wherein each outer edge is spaced at different distances from the centre point, and wherein each of the plurality of calibration features is an aperture formed through an entire thickness of the holder or is an insert of a transparent or substantially transparent material which is placed into a hole in the holder; and wherein each calibration feature includes an inner edge opposite the outer edge, and wherein the inner edge of each calibration feature is spaced the same radial distance from the centre point.

18. The sample holder of claim 17, wherein the sample holder includes at least four calibration features.

* * * * *